United States Patent [19]

Welker

[11] Patent Number: 5,578,770
[45] Date of Patent: Nov. 26, 1996

[54] APPARATUS AND METHOD FOR GAS DETECTION

[75] Inventor: Brian H. Welker, Sugar Land, Tex.

[73] Assignee: Welker Engineering Company, Sugar Land, Tex.

[21] Appl. No.: 526,233

[22] Filed: Sep. 11, 1995

[51] Int. Cl.$^6$ .................................................. G01N 31/22
[52] U.S. Cl. .................. 73/864.81; 73/863.84; 73/864.62
[58] Field of Search .......................... 73/864.35, 864.63, 73/864.81, 864.62, 863.86, 863.83, 863.85; 422/83, 85, 86

[56] References Cited

U.S. PATENT DOCUMENTS

| | | | |
|---|---|---|---|
| 3,710,626 | 1/1973 | Otte et al. | 73/422 |
| 5,098,847 | 5/1992 | Welker | 73/864.62 |
| 5,379,654 | 1/1995 | Carvajal et al. | 73/863.84 |
| 5,390,551 | 2/1995 | Carvajal et al. | 73/863 |

OTHER PUBLICATIONS

Sensidyne/Gastec "The First Truly Simple Precision Gas Detection System", Sensidyne, Inc., Clearwater, Fl.
Sensidyne "FM, CSA and Cenelec Certified Combustible Gas Detection Systems", Sensidyne, Inc., Clearwater Fl., Dec. 1992.
Sensidyne Pyrotec Pyrolyzer, Sensidyne, Inc., Clearwater, Fl., Jul. 1992.
Sensidyne Portable Gas Detection, Sensidyne, Inc., Clearwater, Fl., Sep. 1993.
Sensidyne BDX 530, Sensidyne, Inc., Clearwater Fl., Jul. 1993.
Sensidyne BDX530$^{CF}$ and BDX530$^{CFT}$, Sensidyne, Inc., Clearwater, Fl., Sep. 1993.
Sensidyne Catalog of Products, Sensidyne, Inc., Clearwater, Fl., Sep. 1991.

*Primary Examiner*—Robert Raevis
*Attorney, Agent, or Firm*—Herzog, Crebs & McGhee, LLP

[57] ABSTRACT

An apparatus and method for use in conjunction with a Dräger tube for the simultaneous testing and storage of a particular gas from a source and the subsequent flaring of the gas after testing is set forth herein. The apparatus generally includes a sample cylinder having two heads closing a chamber with an internal piston delineating two variable volume spaces therein. The front head is threaded to and in selective communication with, by means of valves disposed within channels, a supply line connected to a gas source, a test line with the Dräger tube, and an exhaust line coupled to a flare line. The rear head is threaded to and in selective communication with, by valves disposed within channels, the test shaft and the exhaust line. The gas enters into the first variable volume space when the valve on the supply line is opened. When the valve located on the front head in communication with the exhaust line is opened, the system can be purged of foreign material by repeatedly filling the first variable volume space and then opening the valve. When the first variable volume space is again full, the pair of valves leading to the test line are opened, and the gas passes through the test line and into the second variable volume space, where it is temporarily stored. When the valve leading to the exhaust line is opened, the gas exits the second variable volume space and is flared.

19 Claims, 4 Drawing Sheets

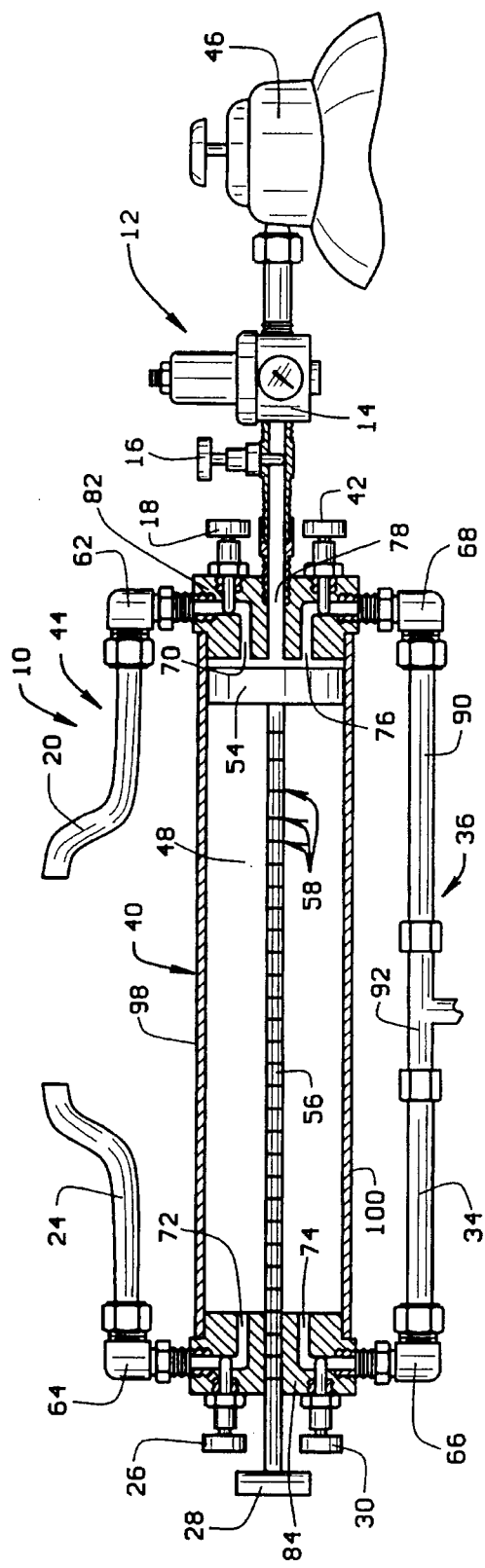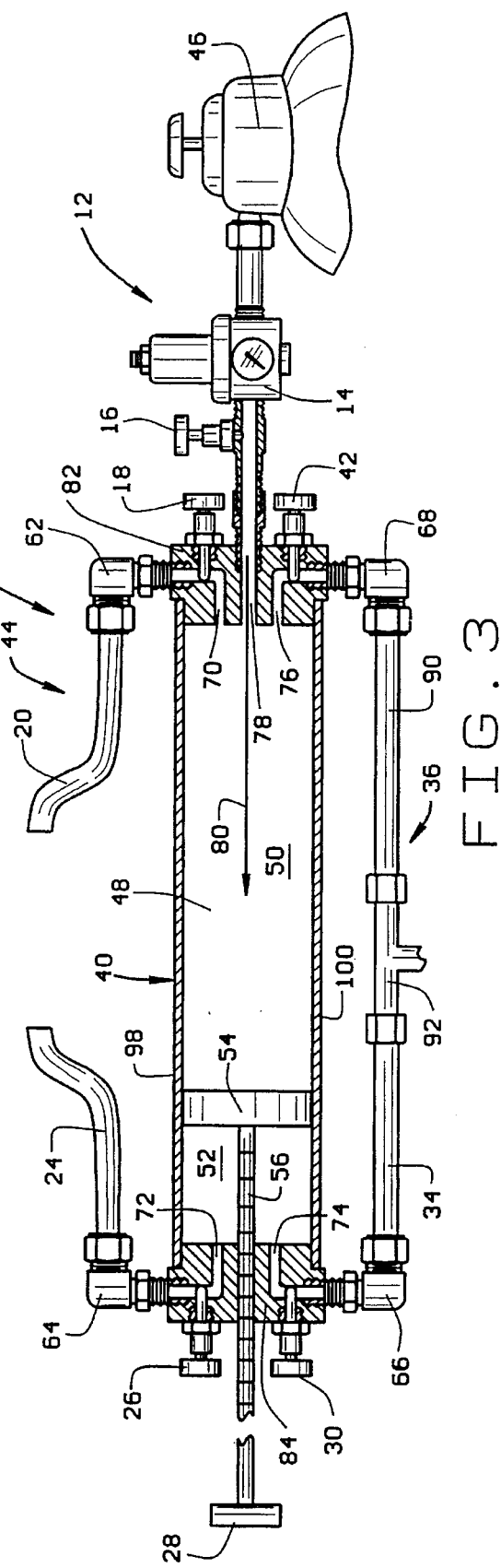

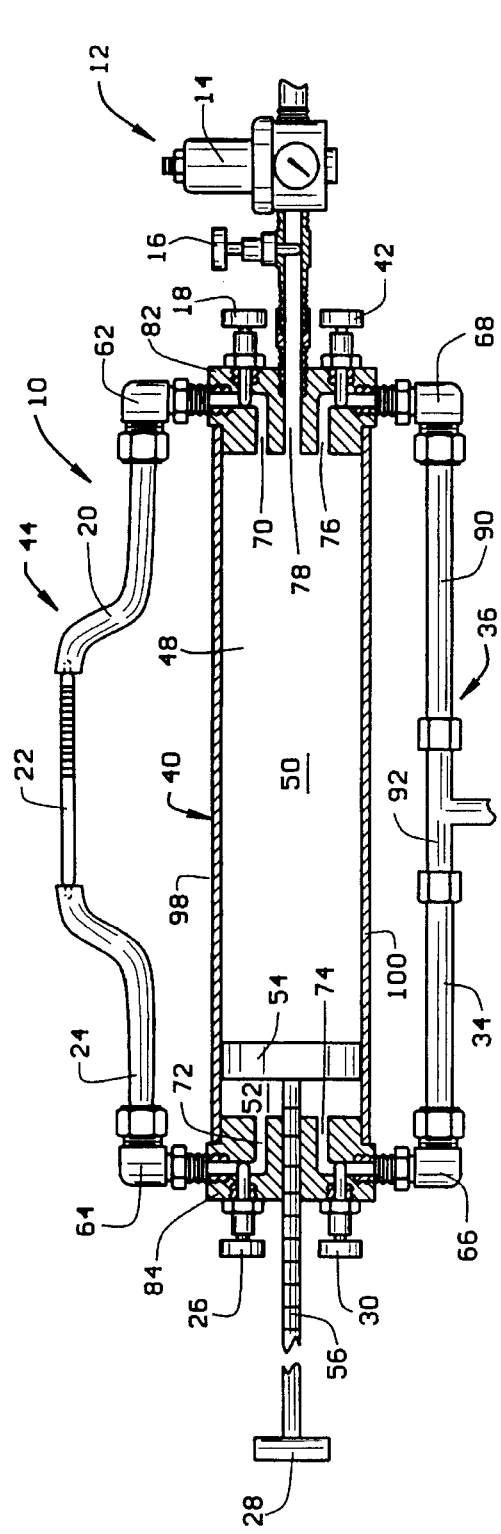
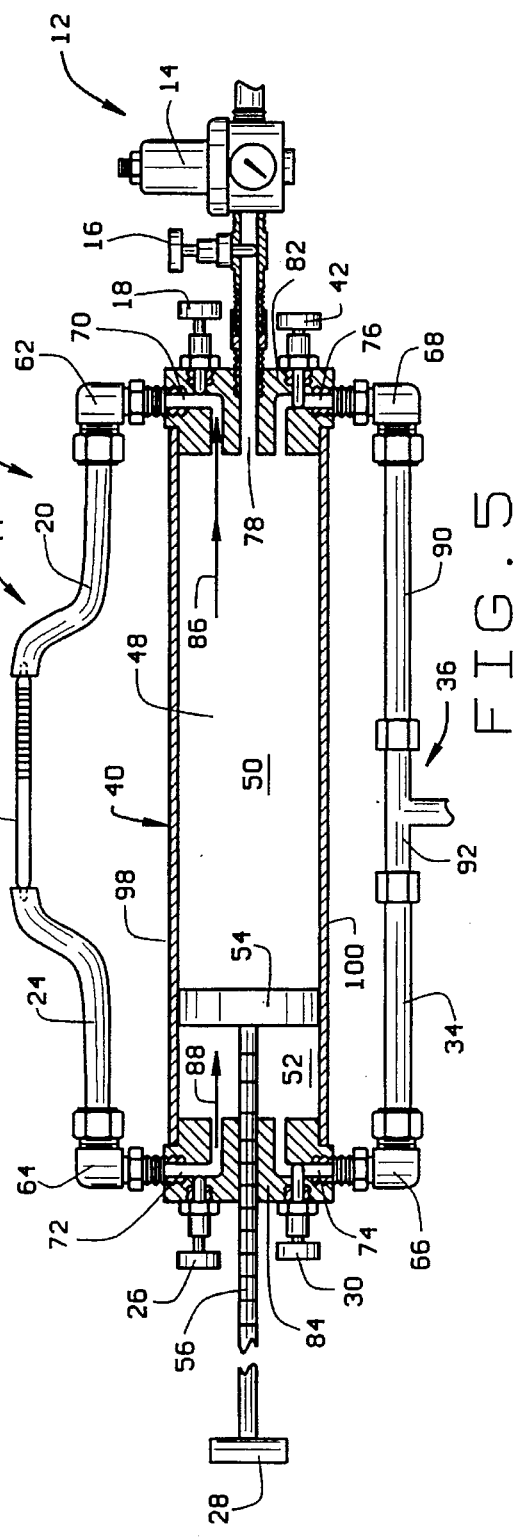

APPARATUS AND METHOD FOR GAS DETECTION

BACKGROUND OF THE INVENTION

1. Field of the Invention

The present invention relates to an apparatus and method for testing the concentration of a particular gas from a source using a length of stain detection device, i.e. a Dräger tube, and more particularly to the storing of the tested gas in the same apparatus for later analysis and the flaring of the gas for disposal.

2. Description of Related Art

It is a common practice in chemical plants to test for hazardous substances such as poisonous hydrogen sulfide gas in samples taken from process lines, petroleum storage tanks and other confined spaces. For sampling, typically five gas detection apparatus are used to collect separate gas samples from the same source. Of these five, two are run through a Dräger tube, discussed below, to determine the concentration of the particular gas tested. The other three samples are saved in the apparatus for up to three to five years for further analysis. A shortcoming of this method of sampling, however, is the great expense incurred because of the necessity of purchasing five gas detection apparatus for each test. The expense would be sharply reduced if a single gas detection apparatus both ran the gas sample though the Dräger tube and stored the gas after testing.

A gas detection apparatus that is representative of the type used for the above sampling is disclosed by U.S. Pat. No. 5,098,847, entitled METHOD AND APPARATUS FOR PORTABLE TESTING OF PRODUCTS FROM PROCESSING COLUMN issued to Welker Mar. 24, 1992. The '847 patent teaches a portable test apparatus in which the gas sample is collected within a cylinder defining a chamber and having a movable piston coupled to a piston rod therein. A passage that is selectively vented to the atmosphere by means of a first valve is positioned behind the piston rod, such that when the first valve is opened, the piston is able to move within the chamber. The chamber is connected to a process line with a second valve positioned therebetween, which when opened fills the cylinder with the gas from the process line while displacing the piston back within the chamber. When the chamber is full, a third valve leading to a valve connection port with a Dräger tube is opened. A Dräger tube is a length of stain detection device containing a reagent specifically sensitive to a particular vapor or gas. When in use, the hermetically-sealed two ends of the Dräger tube are broken and one end is placed in selective communication with the gas to be sampled, in this case the valve connection port. With the third valve open, the piston rod is manually pushed forward, thereby forcing the gas sample through the Dräger tube and out into the atmosphere.

Due to an increased awareness of the environmental considerations associated with the emitting of gaseous fluids and other toxins into the atmosphere, the government is now requiring companies to flare all potentially toxic gaseous substances, such as those tested with gas detection systems in chemical plants, instead of merely venting the hazardous substances to the atmosphere. As a result, while there are readily available apparatus for testing the concentration of a particular gas in a sample, such as the one described above, there has yet to be developed an apparatus which provides a system for discharging the gas sample to a flare line as opposed to the atmosphere.

With the above considerations in mind, it is an object of the present invention to eliminate the great expense of sampling incurred by purchasing separate gas detection apparatus for the testing and storing of a gas sample by providing a gas detection apparatus which extracts a gas sample from a gas source, tests the gas sample through a Dräger tube, and then stores the gas sample for later analysis.

It is a further object of the present invention to provide an apparatus which vents a gas sample to a flare line as opposed to the atmosphere.

SUMMARY OF THE INVENTION

The present invention is a gas detection apparatus and method to be used in conjunction with a stain detection device such as a Dräger tube which can extract, test, store and flare a gas sample from a gas source. The gas detection apparatus generally includes a sample cylinder having a test line that is adapted to be threaded to and in communication with a supply line and an exhaust line. The sample cylinder has a front head and a rear head which encloses or defines a chamber having a slidably mounted piston located therein. The piston delineates a first and second variable volume space within the chamber with the first variable volume space defined by the area between the piston and the front head and the second variable volume space defined by the area between the piston and the rear head. The piston is coupled to a piston rod which extends through the second variable volume space and beyond the rear head of the sample cylinder. The piston rod is used to move the piston back and forth within the chamber.

The supply line is threadable on one end to the front head of the sample cylinder so as to be in communication with the first variable volume space by means of an inlet channel. The supply line is threaded on its opposite end to the gas source. A process valve is disposed within the supply line to selectively allow the gas from the source to enter into the first variable volume of the sample cylinder. A vent valve is located behind the piston on the rear head of the sample cylinder in selective communication with and disposed between the second variable volume space and the atmosphere. With the vent valve open, the piston is allowed to move back within the chamber when the process valve is opened.

The test line is coupled on one end to the front head of the sample cylinder, in communication with the first variable volume space by means of a channel in the front head. The other end of the test line is coupled to the rear head of the sample cylinder, in communication with the second variable volume space also by means of a channel in the rear head. A test valve is disposed within each of the channels to selectively allow the gas sample to enter and exit the test line.

The exhaust line has three ends, one of which is connectable to a flare line by means of a check valve. The second end is threaded to the front head of the sample cylinder, in communication with the first variable volume space by means of a channel in the front head. A purge valve is disposed within the channel to selectively allow the gas sample to exit the first variable volume space into the exhaust line to purge the first variable volume space of foreign material. The third end is threaded to the rear head of the sample cylinder in communication with the second variable volume space by means of a channel in the rear head. An exhaust valve is disposed within the channel to selectively vent the gas sample from the second variable volume space to the exhaust line.

The method for detecting the concentration of a sample gas from the gas source generally includes providing an apparatus such as the one previously described. First, the sample cylinder is filled by opening the process and exhaust valves and pulling the piston rod back. These valves are then closed, and the system is purged by opening the vent valve and the purge valve and discharging the gas to the flare line by pushing the piston forward. The steps of filling the cylinder and discharging the gas to the flare line is done repeatedly to completely purge the system.

After purging, the process valve is opened and the cylinder is filled to a predetermined volume with the gas in the first variable volume space. The process valve is then closed and the piston is pulled completely back to allow the gas to expand to the entire volume of the chamber. When the piston rod is at the rear head of the sample cylinder, the vent valve is closed.

Next, the gas is tested by opening the pair of test valves and pushing the piston rod completely inward to force the gas through the Dräger tube via the test line and into the second variable volume space. The test valves are then closed, and the gas is temporarily stored within the second variable volume space of the sample cylinder. After reading the length of stain on the Dräger tube, the Dräger tube is removed and discarded.

To dispose of the gas sample stored in the second variable volume space, the exhaust valve is opened. The gas is vented to the exhaust line and into the flare line.

BRIEF DESCRIPTION OF THE DRAWINGS

The above-mentioned and other features, advantages and objects of this invention, in the manner in which they are obtained, will become more apparent and will be best understood by reference to the detailed description in conjunction with the accompanying drawings which follow, wherein:

FIG. 2 is a cross-sectional view of the gas detection apparatus of FIG. 1 before a gas sample is taken, showing a piston positioned at the front head of a sample cylinder;

FIG. 3 is a cross-sectional view of the gas detection apparatus of FIG. 1 while a gas sample is being taken, showing the process valve open and the gas entering the sample cylinder and pushing back the piston;

FIG. 4 is a cross-sectional view of the gas detection apparatus of FIG. 1 after the first variable volume is full, showing the process valve closed and the piston at the rear head of the sample cylinder;

FIG. 5 is a cross-sectional view of the gas detection apparatus of FIG. 1 while the gas is being tested, showing both test valves open and the gas entering through one end of the test line and exiting from the other end of the test line and back into the sample cylinder.

DESCRIPTION OF THE PREFERRED EMBODIMENTS

Figure 1:
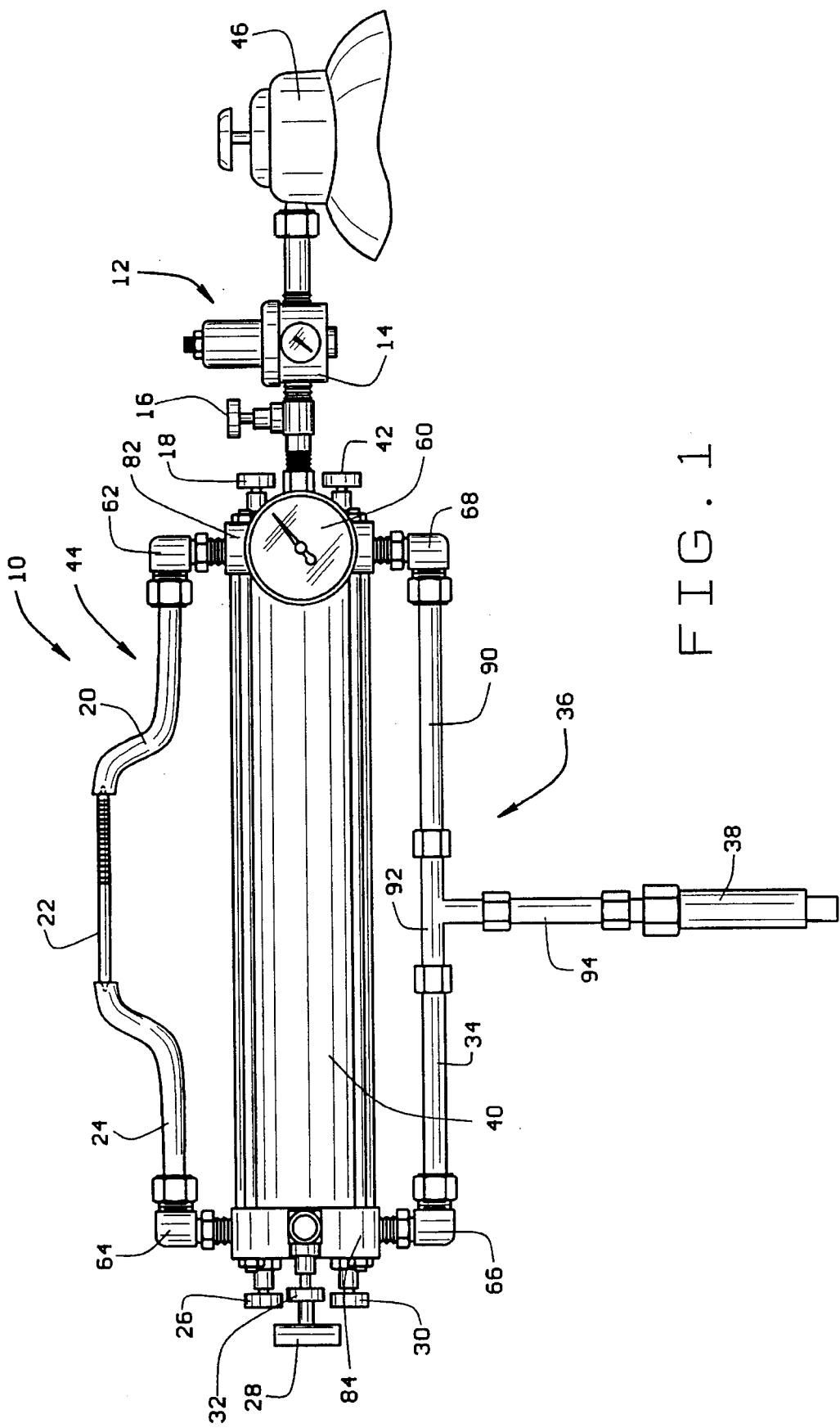
FIG. 1 is a perspective view of the gas detection apparatus of the present invention attached to a storage tank.
Figure 6:
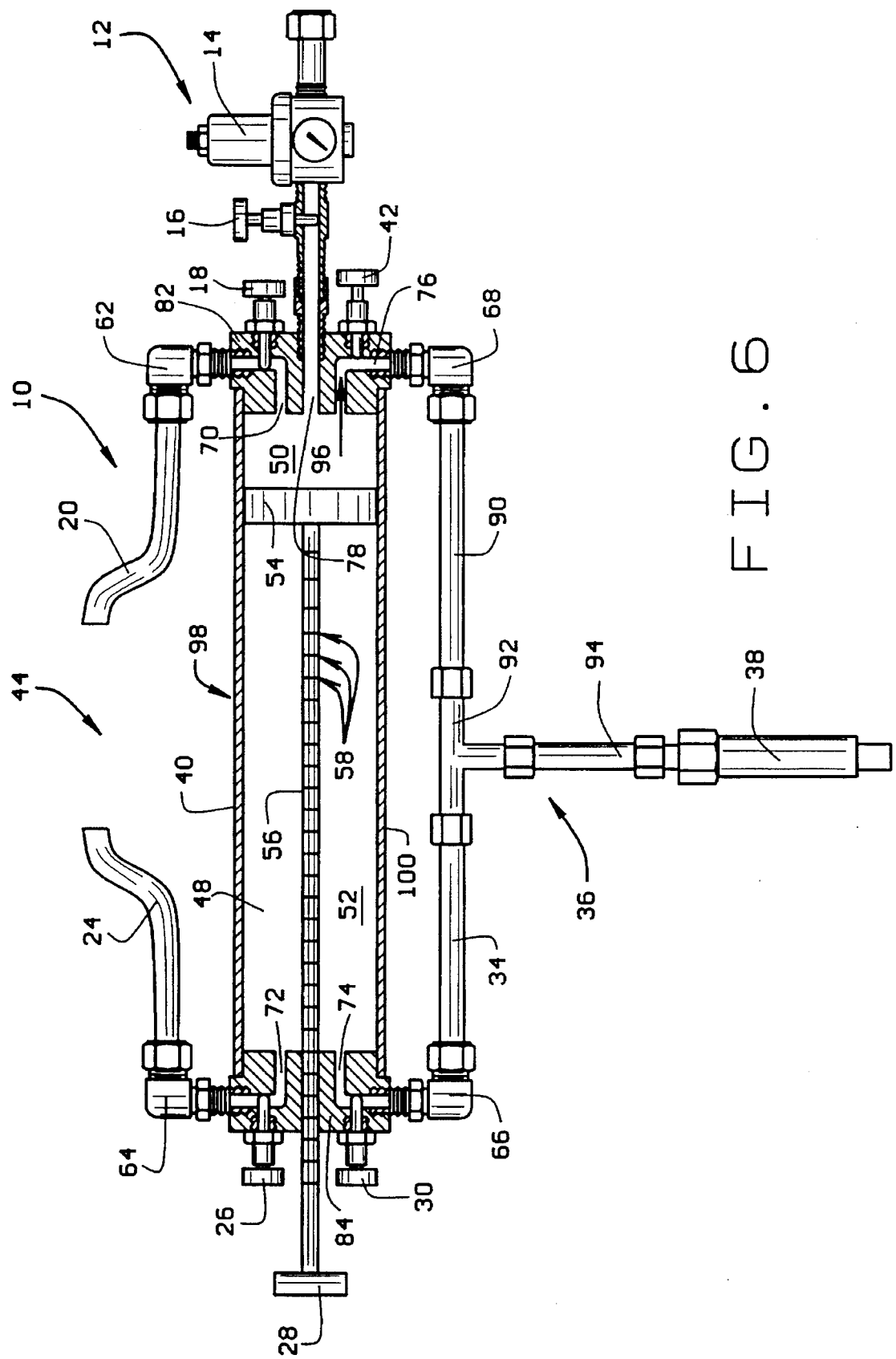
FIG. 6 is a cross-sectional view of the gas detection apparatus of FIG. 1 while being purged, showing the gas exiting the purge valve and into the exhaust line.

Referring to FIG. 1, a gas detection apparatus 10 is shown that generally includes a sample cylinder 40, a test line 44, a supply line 12 and an exhaust line 36. The gas detection apparatus 10 is used in conjunction with a Dräger type tube 22, which is a hermetically-sealed tube of glass with a reagent therein, also known as a "length of stain detector." In order to use the Dräger tube 22, one breaks the opposite ends of the tube thereby exposing the reagent to the gas that is to be tested for a specific substance, for example, hydrogen chloride or hydrogen sulfide. The reagent reacts to the particular substance and instantly changes color quantitatively to provide a length-of-stain indication. The length-of-stain indication corresponds the concentration of the particular gas being tested for.

The sample cylinder 40 generally has a front head 82 and a rear head 84, closing and defining a chamber 48 therein. As best seen in FIGS. 2–6, the front head 82 of sample cylinder 40 has an inlet channel 78 which communicates with the source of the gas by means of supply line 12. The supply line 12 is threadably attached at one end to the front head 82 to communicate with the inside the sample cylinder 40. The other end of the supply line 12 is coupled to the source of the gas to be tested, e.g. a storage tank 46 or other confined area, such as a pipeline or a transportation tank. A process valve 16 is threadedly disposed along the supply line 12 which, when opened, clears the passageway to the inlet channel 78 and allows the gas to enter the chamber 48 of the sample cylinder 40. A regulator 14 is threaded between the process valve 16 and the storage tank 46 to monitor the pressure of the gas from the storage tank 46 that enters into the sample cylinder 40. In the preferred embodiment, the regulator 14 controls the pressure of the gas to approximately 10 pounds per square inch. The pressure of the gas within the chamber 48 is also continuously monitored by a cylinder pressure gauge 60 (FIG. 1). In the preferred embodiment, the pressure within the chamber 48 is maintained at 10 pounds per square inch.

A piston 54 is slidably mounted within the chamber 48 and delineating a first variable volume space 50 and a second variable volume space 52. The piston 54 supports appropriate seals (not shown) on its exterior to tightly seal the piston within the chamber 48. As best seen in FIG. 3, the first variable volume space 50 is defined by the area between the piston 54 and the front head 82 of the sample cylinder 40, and the second variable volume space 52 is defined by the area between the piston 54 and the rear head 84 of the sample cylinder 40. A piston rod 56 threads or joins to the piston 54 and extends through the second variable volume space 52. The rod 56 moves through appropriate seals (not shown) on the rear head 84 of the sample cylinder 40 and extends beyond the sample cylinder 40, terminating in a handle 28. The rod 56 is graduated, having calibration markings 58 at regular distances indicative of a specified volume to which the first variable volume space 50 can be filled. In the preferred embodiment, a stop position marking (not shown) defines when the first variable volume space 50 is 65–70% full at 10 pounds per square inch.

The test line 44 comprises two flex hoses 20 and 24, each of which is coupled at one end into elbow fittings 62 and 64, respectively. The other end of each flex hose 20, 24 is open for coupling to the Dräger tube. The elbow fittings 62 and 64 are of the standard type known in the art, having a hollow externally threaded bolt member extending from one end, and a hollow internally threaded nut member extending from the other end. The elbow fitting 62 is threaded on the top side 98 of the front head 82 of the sample cylinder 40, in fluid communication with the first variable volume space 50 by means of a channel 70. The elbow fitting 64 is threaded on the top side 98 of the rear head 84 of the sample cylinder 40, in fluid communication with the second variable volume space 52 by means of a channel 72. The channels 70 and 72 have test valves 18 and 26 respectively, disposed therein for selective communication of the gas sample to and from the test line 44.

The exhaust line 36 generally includes three linear members 34, 90 and 94 fabricated of a hard tubing material. Each linear member is coupled at a respective end to a T-shaped member 92 by means of threaded nuts or other fasteners as commonly known in the industry. The exhaust line 36 is bolted at the opposite ends of the linear members 34 and 90 into the elbow fittings 66 and 68, respectively, each having the same characteristics as the elbow fittings 62 and 64. The elbow fitting 68 is threaded on the bottom side 100 of the front head 82 of the sample cylinder 40, in fluid communication with the first variable volume space 50 by means of a channel 76. The elbow fitting 66 is threaded in the bottom side 100 of the rear head 84 of the sample cylinder 40, in fluid communication with the second variable volume space 52 by means of a channel 74. The channels 76 and 74 have a purge valve 42 and an exhaust valve 30, respectively, disposed therein for selective communication of the gas to the exhaust line 36 from the first and second variable volume spaces 50 and 52, respectively. In order to prevent the gaseous fluids and toxins to vent into the atmosphere from the exhaust line 36, the exhaust line 36 is connected to a flare line (not shown) by means of a check valve 38 coupled to the opposite end of extension member 94.

The testing or operation sequence of the gas detection apparatus 10 occurs in the following manner. This will be described in conjunction with FIGS. 2–6. First, prior to testing, the piston 54 is positioned all the way to the front end 82 of the sample cylinder 40. All valves 16, 18, 26, 30, 42 are closed, as in FIG. 2, with the check valve 38 on the exhaust line 36 connected to a flare line (not shown). The pressure of the gas sample from the supply line 12 is controlled to substantially 10 pounds per square inch.

Next, as shown in FIG. 3, the process valve 16 is opened slowly while the user observes the piston rod handle 28. If the handle 28 moves, the user applies hand pressure to the rod to control the piston movement to contact the flow of gas into the first variable volume space 50. The process valve 16 is then fully opened along with the exhaust valve 30. The piston rod 56 is pulled back until it stops on the rear head 84. At this point, the first variable volume space 50, now equal to the sample cylinder volume 40, is full.

After the sample cylinder 40 has been filled, the process valve 16 and the exhaust valve 30 are closed. The purge valve 42 is then opened and the gas is discharged through the exhaust line 36 and to the flare line by pushing the piston 54 forward, as shown by arrow 96 in FIG. 6. The system is purged of foreign material by repeatedly opening the process valve 16 and filling the sample cylinder 40, closing the process valve 16, and finally opening the purge valve 42 and pushing the piston 54 forward. Because inward movement of the piston 54 from the gas from the supply line 12 builds an opposing pressure which must be vented in order to fill the sample cylinder 40, a vent valve 32 in communication with the atmosphere and the second variable volume space 52 is provided and opened for this end. Alternatively, the test valve 26 can be opened for this purpose because hose 24, which has not yet been coupled to the Dräger tube 22, also communicates with atmospheric air.

Once the system is fully purged, the process valve 16 is opened slowly with the vent valve 32 or test valve 26 still open while the user once again observes the piston rod handle 28 for movement. If the handle 28 moves, hand pressure is applied to the rod 56 to control the movement of the piston 54. The process valve 16 is then fully opened to allow the gas to enter the first variable volume 50 of the sample cylinder 40, as shown by arrow 80 in FIG. 3, while pushing back the piston 54 a predetermined distance. The calibration markings 58 are used to accomplish this end by pulling the piston rod handle 28 out until the desired calibration marking emerges from the rear end 84 of the sample cylinder 40. As previously stated in the preferred embodiment, the desired calibration marking is a stop position marking (not shown) positioned along the rod 56 to define when the sample cylinder 40 is approximately 65–70 percent full of the gas sample in the first variable volume space 50.

At this point, the cylinder pressure gauge 60 is observed. If the pressure is not atmosphere, the user opens the purge valve 42 to dump the sample. The pressure on the regulator 14 of the supply line 12 is then adjusted to compensate. If the pressure is atmosphere, a Dräger tube 22 is then coupled to flex hoses 20 and 24. The piston 54 is pulled completely back to the rear head 84 of the sample cylinder 40 to allow the gas to expand to the entire volume of the chamber 48, as shown by FIG. 4. The vent valve 32 is then closed.

Next, the gas is tested. The testing process is best illustrated in FIG. 5. When the test valves 18 and 26 are opened, the passageways of channels 70 and 72 are cleared. The piston rod 56 is pushed inward and the piston 54 forces the gas sample from the first variable volume space 50 into the test line 44, as represented by arrow 86, through the Dräger tube 22, and then out of the test line 44 and into the second variable volume space 52, as indicated by arrow 88. While pushing in the rod 56, the cylinder pressure gauge 60 is continuously observed. The rod 56 is pushed inward at a rate such that the pressure within the sample cylinder 40 does not exceed one or two pounds per square inch.

After the piston reaches the front head 82 of the sample cylinder 40, the test valves 18 and 26 are closed, and the gas is stored within the second variable volume space 52 of the sample cylinder 40. The Dräger tube 22 is then read, removed from the flex hoses 20 and 24, and finally discarded.

To dispose of the stored gas, the exhaust valve 30 is opened, thereby clearing the passageway of the channel 74 for gas flow from the second variable volume space 52 through the exhaust line 36 and into the flare line (not shown).

Accordingly, while this invention is described with reference to a preferred embodiment of the invention, it is not intended to be construed in a limiting sense. It is rather intended to cover any variations, uses or adaptions in the invention utilizing its general principles. Various modifications will be apparent to persons skilled in the art upon reference to this description. It is therefore contemplated that the appended claims will cover any such modifications or embodiments as fall within the true scope of the invention.

What is claimed is:

1. An apparatus used in conjunction with a gas detection tube that has a front end and a back end that are each opened when the gas detection tube is used for testing the concentration of a gas sample from a gas source, the apparatus comprising:

a) a sample cylinder defining a chamber;

b) a piston slidably mounted within said chamber of said sample cylinder, said piston delineating a first variable volume space and a second variable volume space within said chamber;

c) a piston rod coupled to said piston for displacing said piston within said chamber;

d) a process valve disposed between and in selective fluid communication with said first variable volume space and the gas source for selectively filling said first variable volume space with the gas sample;

e) a purge valve disposed between and in selective fluid communication with said first variable volume space and a flare line for selectively purging said first variable volume space of foreign material;

f) a pair of test valves, the first of said test valves disposed between and in selective fluid communication with said first variable volume space and the front end of the gas detection tube for selectively introducing the gas sample into the gas detection tube, the second of said test valves disposed between and in selective fluid communication with said second variable volume space and the back end of the gas detection tube for selectively storing the sample after the gas sample has passed through the gas detection tube; and g) an exhaust valve disposed between and in selective fluid communication with said second variable volume space and the flare line for selectively discharging the sample from said sample cylinder.

2. The apparatus of claim 1, further including a gauge for monitoring pressure within said sample cylinder.

3. The apparatus of claim 1, further including a supply line coupled at a first end to said sample cylinder and at a second end to the gas source, wherein said process valve is disposed in said supply line, said supply line further including a regulator disposed between said process valve and the gas source for monitoring the pressure of the gas sample from the gas source.

4. The apparatus of claim 1, further including an exhaust line having a first end in fluid communication with said purge valve, a second end in fluid communication with said exhaust valve, and a hollow lateral tube member disposed between said first end and said second end, said lateral tube member coupled to the flare line.

5. The apparatus of claim 4, further including a check valve disposed between said lateral tube member and the flare line.

6. The apparatus of claim 1, further including a vent valve disposed between and in selective fluid communication with said second variable volume space and the atmosphere for selectively introducing atmospheric air to said second variable volume space.

7. The apparatus of claim 1, further including a pair of hoses, each of said hoses having two open ends, a first one of said hoses coupled at one end to a first one of said test valves and at the other end to the front end of the gas detection tube, a second one of said hoses coupled at one end to a second one of said test valves and at the other end to the back end of the gas detection tube.

8. The apparatus of claim 1, wherein said piston rod includes an exterior end extending beyond the end of said sample cylinder.

9. The apparatus of claim 8, wherein said piston rod further includes a handle disposed on said exterior end.

10. The apparatus of claim 8, wherein said piston rod further includes a plurality of calibration markings.

11. A method for detecting the concentration of a particular gas in a composite gas sample from a supply line, which comprises the steps of:

a) providing a sample cylinder defining a test chamber having a piston disposed therein delimiting a first and second variable volume space within the chamber, wherein the piston is coupled to a piston rod which extends through and beyond the end of the sample cylinder, the piston rod including a plurality of calibration markings, one of the markings defining a stop position;

b) providing a test shaft including a gas detection tube with first and second open ends and filled with a reagent specifically sensitive to a particular gas, said first and second open ends of the gas detection tube inserted into respective first and second hoses, the first hose connected to a first test valve in selective fluid communication with the first variable volume space, the second hose connected to a second test valve in selective fluid communication with the second variable volume space;

c) providing an exhaust valve disposed between and in selective fluid communication with the second variable volume space and a flare line;

d) providing a purge valve disposed between and in selective fluid communication with the first variable volume space and the flare line;

e) providing a vent valve disposed between and in selective communication with the atmosphere and the second variable volume space;

f) providing a process valve disposed between and in selective communication with the supply line and the first variable volume chamber;

g) opening the process valve;

h) opening the exhaust valve;

i) pulling the piston rod back until the sample cylinder is full;

j) closing the exhaust valve and the process valve;

k) opening the vent valve;

l) purging the system by repeatedly opening the process valve and pulling the piston rod back to fill the sample cylinder, closing the process valve, opening the purge valve, pushing the piston rod forward to discharge the gas to the flare line, and closing the purge valve;

m) opening the process valve;

n) pulling the piston rod handle back until the marking defining the stop position is aligned with the end of the sample cylinder;

o) closing the process valve;

p) pulling the piston rod back completely by allowing it to pass by the stop position marking;

q) closing the vent valve;

r) opening both the first and second test valves;

s) pushing the piston rod inward all the way to the end to force the entire gas sample through the test shaft and into the second variable volume space;

t) closing both the first and second test valves;

u) reading the gas detection tube;

v) removing and disposing of the gas detection tube; and w) opening the exhaust valve, thereby discharging the gas sample into the flare line.

12. The method of claim 11, further comprising the steps:

a) providing a regulator on the supply line; and b) controlling the pressure of the gas sample from the gas source.

13. The method of claim 12, further including the steps of:

a) providing a cylinder pressure gauge;

b) observing the cylinder pressure gauge after step (o).

14. The method of claim 13, further including the steps of:
a) opening the purge valve, thereby dumping the sample; and
b) adjusting the pressure on the regulator on the supply line to compensate if the pressure is not atmosphere.

15. The method of claim 13, further including the steps of:
a) observing the cylinder pressure gauge continuously during step (s);
b) pushing the piston rod inward at a rate such that the cylinder pressure does not exceed 1 or 2 pounds per square inch as observed on the cylinder pressure gauge.

16. The method of claim 12, wherein the pressure of the gas sample from the gas source is controlled to substantially 10 pounds per square inch.

17. The method of claim 11, wherein the marking defining the stop position is positioned to define when the sample cylinder is approximately 65–70 percent full with the gas sample in the first variable volume space at 10 pounds per square inch.

18. The method of claim 11, further including the step of observing the piston rod for movement after the process valve is opened in steps (g) and (m).

19. The method of claim 18, further including the step of applying hand pressure to the piston rod to prevent the movement of the piston rod if the piston rod moves.

* * * * *